United States Patent
Willoughby et al.

(10) Patent No.: US 8,512,303 B2
(45) Date of Patent: Aug. 20, 2013

(54) NEGATIVE DRAWSTRING SEAL FOR AN OSTOMY BAG

(75) Inventors: Alastair Willoughby, Cambridge (GB); Mark Rogers, North Lincs (GB); Gary Stacey, Cambridge (GB); Wai Chan, Harston (GB)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/697,014

(22) PCT Filed: May 10, 2011

(86) PCT No.: PCT/DK2011/050158
§ 371 (c)(1),
(2), (4) Date: Nov. 9, 2012

(87) PCT Pub. No.: WO2011/141029
PCT Pub. Date: Nov. 17, 2011

(65) Prior Publication Data
US 2013/0060214 A1 Mar. 7, 2013

(30) Foreign Application Priority Data
May 10, 2010 (DK) .................................. 2010 70197

(51) Int. Cl.
*A61F 5/44* (2006.01)
(52) U.S. Cl.
USPC ............................. 604/338; 604/337; 604/339
(58) Field of Classification Search
USPC .......................................... 604/337, 338, 339
See application file for complete search history.

(56) References Cited

U.S. PATENT DOCUMENTS

| 3,685,786 | A | 8/1972 | Woodson | |
|---|---|---|---|---|
| 6,589,167 | B1 | 7/2003 | Shimomura et al. | |
| 6,974,090 | B2 | 12/2005 | Brax | |
| 7,819,800 | B2* | 10/2010 | Beckman et al. | 600/208 |
| 8,137,267 | B2* | 3/2012 | Shelton et al. | 600/203 |
| 8,202,252 | B2* | 6/2012 | Ross | 604/167.06 |
| 2002/0002324 | A1 | 1/2002 | McManus | |
| 2008/0146882 | A1* | 6/2008 | Cropper et al. | 600/206 |
| 2008/0146884 | A1 | 6/2008 | Beckman et al. | |
| 2008/0221389 | A1* | 9/2008 | Beckman et al. | 600/114 |
| 2013/0053803 | A1* | 2/2013 | Willoughby et al. | 604/337 |

FOREIGN PATENT DOCUMENTS

| EP | 0381393 | 8/1990 |
|---|---|---|
| GB | 2023007 | 12/1979 |
| WO | 9817212 | 4/1998 |
| WO | 9853771 | 12/1998 |

* cited by examiner

*Primary Examiner* — Tatyana Zalukaeva
*Assistant Examiner* — Jordan B Bailey
(74) *Attorney, Agent, or Firm* — Coloplast Corp., Coloplast A/S; Nick Baumann

(57) ABSTRACT

An ostomy body side member with a sealing member is provided. The sealing member has a fixed base member defining an opening having a first diameter and a resilient sealing element comprising a stoma receiving orifice defining an inner boundary. The inner boundary of the stoma receiving orifice has a second diameter that is smaller than the first diameter of the frame. The sealing member is also provided with at least one adjustment member coupled between the fixed base member and the resilient sealing element. Furthermore, an alignment member for adjusting the tension of the at least one adjustment member is provided thereby allowing the diametrical dimension of the stoma sealing orifice to be adjusted from a first diameter to a second diameter.

11 Claims, 2 Drawing Sheets

NEGATIVE DRAWSTRING SEAL FOR AN OSTOMY BAG

The invention relates to a seal for an ostomy bag which seals by means of a diaphragm contracting like an iris. Furthermore, the invention relates to an ostomy bag including such a seal.

BACKGROUND

The present invention relates to an ostomy appliance and to a method of sealing an ostomy appliance body side member around a stoma. In connection with surgery for a number of diseases in the gastro-intestinal or urinary tract, a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening. Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is permanently attached to the base plate. In case of a two-piece appliance, the adhesive barrier member forms part of a body side member and a receiving member or bag is attached releasably to the body side ostomy member for receiving exudates from the stoma. When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may for example be a system known per se comprising matching coupling rings or matching flanges and adhesive surfaces engaging with and sealing against a flange area of the body side member.

It is necessary to change the body side member of a two-piece appliance when the centre part of the adhesive wafer has been sufficiently deteriorated to allow access of the aggressive exudates to the skin surrounding the stoma, irrespective of the fact that the wafer as such has a much longer wearing time. The access of aggressive exudates to the skin is causing skin problems. Frequent changing of the body side member of a two-piece appliance is undesirable due to the irritation of the skin. The user's quality of life may be improved and the irritation of wearing an ostomy appliance reduced if the intervals between replacing the body side member can be increased.

The service time of the body side ostomy member depends inter alia on the amount and the aggressiveness of the exudates and of the sealing between the stoma and the body side ostomy member. The sealing depends on the fit to the stoma. Conventionally, only a limited number of standard appliances having holes of different sizes are available, and the user or an assistant must customise the body side member by cutting the edge of the hole to adapt the body side member to the stoma.

When cutting the edge of the hole of an adhesive wafer of a conventional one-piece ostomy appliance for adapting it to the size and shape of a stoma, the cutting is complicated by the fact that in order to secure discretion, for decorative purposes and for providing softness, low noise generation and comfort, the bag is often made from an opaque material or covered and/or provided with a cover or front layer rendering it very difficult, if not impossible, for the user or the nurse to observe the stoma area during determination of a cutting line, for adaptation of the hole, or when applying the appliance.

SUMMARY OF THE INVENTION

The invention concerns a seal in a wafer for an ostomy appliance. The sealing member comprises a fixed base member and a resilient sealing element attached to the fixed base member. The sealing member further comprises an adjustment member coupled between the fixed base member and the resilient sealing member. The adjustment member in cooperation with an alignment member allows adjustment of the inner diameter of the resilient sealing member. Thereby a mechanical sealing member is achieved, which makes it possible to use the sealing member with one-piece ostomy appliances as well as two-piece ostomy appliances.

DETAILED DESCRIPTION OF THE INVENTION

A first aspect of the invention relates to an ostomy body side member having a sealing member where the sealing member comprises a fixed base member defining an opening having a first diameter, a resilient sealing element comprising a stoma receiving orifice, defining an inner boundary where the inner boundary of the stoma receiving orifice has a second diameter that is smaller than the first diameter of the frame, at least one adjustment member coupled between the fixed base member and the resilient sealing element, and an alignment member for adjusting the tension of the at least one adjustment member so that the diametrical dimension of the stoma sealing orifice may be adjusted from a first diameter to a second diameter.

The fixed base member provides a supporting mechanism for the resilient sealing member so that the dimensions of the stoma receiving orifice of the resilient sealing member may be adjusted using the at least one adjustment member. This means that the user can adjust the dimensions of the stoma receiving orifice to fit around the stoma so that the sealing member provides a suitable seal around the stoma so that the risk that harmful exudates from the stoma can come into contact with the skin of the user is minimised, as the exudates may irritate or damage the skin surrounding the stoma, and this irritation or damage may be painful for the user.

The adjustment member is coupled between the fixed base and the resilient sealing element so that when tension is applied to the adjustment member, the tensional forces transfer into the resilient sealing member and causes the resilient sealing member to contract, thus increasing the diametric dimension of the stoma receiving opening defined by the resilient sealing member. The opposite effect may be applicable to the resilient sealing member so that when the tension to the adjustment member is reduced, the diametric dimension of the stoma receiving orifice is reduced.

The resilient sealing member may be fabricated from a resilient memory material so that when the resilient sealing member is in its neutral position, i.e. when the memory material is in its initial position or has the shape that is defined by the material's memory, where the diametric dimensions of the stoma receiving orifice is in its first diameter and is brought out of its neutral position, changing the diametric dimensions of the stoma receiving opening to its second diameter, the memory of the material will attempt to return the resilient sealing member to its neutral position, i.e. the starting point. The memory of the material will ensure that when the resilient sealing member is not in its neutral position, the memory characteristics of the resilient material will exert a tension to the adjustment member, and the adjustment member would ensure that the deformation of the resilient sealing member is maintained in its deformed position.

A wafer as described above provides a sealing wafer which is particularly suitable for use with a stoma, as one of the most challenging issues facing users is to ensure that no leaks occur between the stoma and an ostomy wafer, because the stoma output may be seen as very unhealthy for the skin surrounding the stoma.

Moreover, such a sealing wafer can be used for many different sizes and types of uneven skin surfaces around a stoma, and thus the need to provide many different sealing wafers in order to accommodate many different stomas is significantly reduced.

In one embodiment of the present invention, the first diameter of the stoma sealing orifice may be larger than the second diameter of the stoma sealing orifice. In this way, the tension applied to the sealing member, as described above, has been applied prior to the use of the sealing wafer. Thus, the user can apply the sealing wafer around the stoma and decrease the diameter of the sealing member using the rotating member until the stoma sealing orifice is of a suitable dimension to fit around the stoma, while providing a seal around it.

In one embodiment of the present invention, the first diameter of the stoma sealing orifice may be smaller than the second diameter of the stoma sealing orifice. In this way, the base member and the rotation member, as described above, may be in a neutral position relative to each other, meaning that there is no tension within the sealing member. Thus, by applying rotational forces to the rotation member, the dimensions of the stoma sealing orifice may be increased during application, until the stoma sealing orifice is of a suitable dimension to fit around the stoma, while providing a seal around it.

In another embodiment, the dimensions of the stoma receiving orifice may be increased or decreased at will so that a continuous adjustment may be made to ensure that the sealing member provides an effective seal around the stoma.

In one embodiment of the present invention, the at least one adjustment member may be adjustably coupled between the fixed base member and the resilient sealing element so that the tension of the adjustment member may be varied. This means that the user can vary the tension in the at least one adjustment member so that the diametrical dimensions of the stoma receiving orifice of the resilient sealing member may be adjusted according to the user's needs upon the adjustment of the adjustment member.

In one embodiment of the present invention, the wafer may comprise locking means for fixing the position of the adjustment member relative to the fixed base member. The provision of locking means ensures that when the user has found the correct dimension of the stoma receiving orifice, the sealing member may be locked in the correct dimension so that the adjustment member does not lose any tensional forces due to a deformation of the resilient sealing member which may constrict the stoma or so that it does not involuntarily increase the tension in the adjustment member causing the seal between the sealing member and the stoma to break.

In one embodiment of the present invention, there may be two or more adjustment members coupled between the fixed base member and the resilient sealing element. The provision of two or more adjustment members means that the tension in the adjustment member due to the deformation of the resilient sealing member can be distributed into more than one adjustment members, which ensures that if the resilient sealing member is deformed in a specific manner, there is less tension in each of the adjustment members compared to having fewer adjustment members for the same deformation, which reduces the risk that the tension damages the adjustment member, by for example breaking or deforming the adjustment member.

In one embodiment of the present invention, the two or more adjustment members may be arranged substantially at equal radial distances from each other around the stoma sealing orifice of the resilient sealing element. By arranging the adjustment members around the stoma sealing orifice, the deformation of the resilient sealing member may be applied from more than one point around the stoma receiving orifice so that any change in the diametric dimensions of the orifice are provided at more than one point. When using 4-8 adjustment members which are uniformly distributed around the stoma receiving opening, the diametric dimensions of the stoma receiving opening may be varied in a uniform manner so that the opening will be substantially circular around the stoma.

In one embodiment of the present invention, the fixed base member and the alignment member may be in the form of a first ring and a second ring, respectively, where the second ring or the fixed base member is arranged to rotate relative to the first ring or the alignment member. This means that if the alignment member is rotated relative to the fixed base member, the tension in the at least one adjustment member is either increased or decreased, causing the diametrical dimensions of the stoma receiving opening to change from a first diameter to a second diameter.

In one embodiment of the present invention, the fixed base member and the alignment member may be arranged having a ratchet enabling click-wise rotation of the alignment member relative to the fixed base member. This click-wise rotation ensures that the user may rotate the alignment member incrementally, without having visual confirmation about the position of the alignment member. The click function may be felt or heard during the rotation so that the user knows when the alignment member has been moved a specific distance. This is advantageous when the user needs to adjust the sealing member in a public place so that he/she does not have to remove clothing to adjust the seal between the sealing member and the stoma.

In one embodiment of the present invention, the resilient sealing element may be an elastomer membrane, sheet or tube. By using a membrane sheet or a tube, the sealing member may be folded in such a way that a first peripheral end of the proximal side member of the sealing member superimposes a second peripheral end of the distal side member of the sealing member, and the folding line or folding bend between the proximal and the distal side members defines the stoma sealing orifice. The adjustment member may be coupled to the folding line or folding bend of the resilient sealing element so that any tension applied to the adjustment member will result in the deformation of the resilient sealing element and cause the folding line or the folding bend to move in a radial direction relative to the fixed base member and/or the alignment member.

In one embodiment of the present invention, the resilient sealing element may be a Silicone, rubber, thermoplastic elastomer, a Dow Corning 30 Shore A silicone type or any suitable elastomeric material. The suitability of the elastomeric material depends on how well the material tolerates output from the stoma, the flexibility and resilience of the material ensuring that the tension applied to the material does not permanently deform the material and ensuring that the material will return to its natural position when no tension is applied to it. The specific choice of material may be obvious to the skilled person, based on the teachings of the present invention.

A second aspect of the invention relates to an ostomy appliance comprising a sealing member as described above and an ostomy collecting bag attachable to the distal surface of the attachment platform.

In one embodiment of the ostomy appliance, the ostomy collecting bag may be attached to the distal surface of the attachment platform by an adhesive coupling.

In one embodiment of the ostomy appliance, the ostomy collecting bag may be attached to the distal surface of the attachment platform by a mechanical coupling.

This invention relates specifically to the sealing member, but also to ostomy appliances that contain such a seal. Although the following description sets out the design of a seal for a two piece appliance (as understood from the prior art) it should be understood that the same principle can be applied to the design of a one-piece appliance.

Such an ostomy collecting bag may be attached to the distal surface of the attachment platform by means of for example an adhesive coupling or a mechanical coupling. Alternatively, the ostomy collecting bag may be permanently attached during manufacturing by for example a weld or glue.

The invention provides users with a seal for their stoma bag with only a single size covering all sizes and shapes of stoma without the need to use a tool such as a scalpel to re-shape the device.

The invention further provides users with a sealing member that can be adjusted to fit, once the user platform is in place.

The invention further provides users with a sealing member that can be adjusted, once the bag is in place and during wear.

The invention further provides users with a sealing member that has adjustment limits so that it is not so tight as to constrict blood flow as this is potentially fatal.

And, the invention further provides users with a sealing member and a user platform in which loads associated with the bag element of the total appliance containing stoma discharge can be passed to the user platform Typically, the attachment platform is in the shape of a disc, having a relatively large surface area in relation to its thickness. The disc can have many shapes, typically annular and circular, but may also have a square, triangular or ellipsoidal shape.

DETAILED DESCRIPTION OF THE DRAWING

Figure 1:
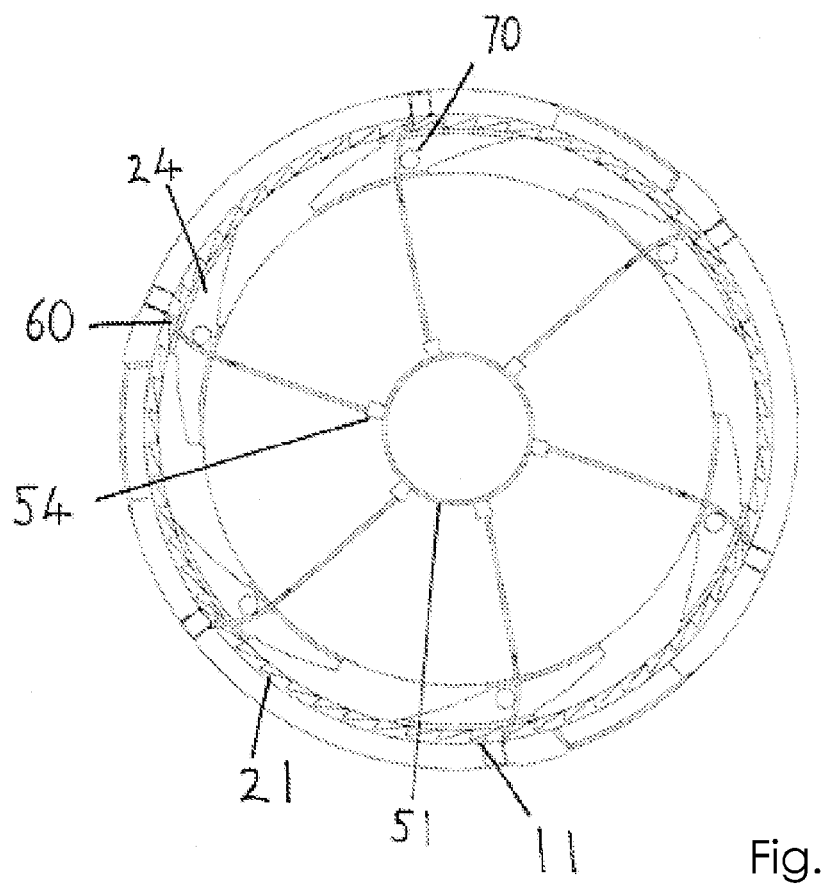
FIG. 1 shows a top view of a sealing member according to the present invention.
Figure 2:
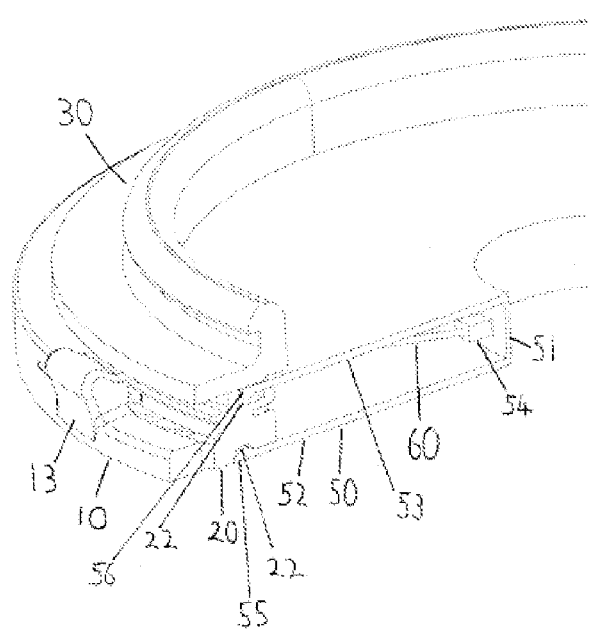
FIG. 2 shows a partial perspective view of a sealing member according to the present invention.
Figure 3:
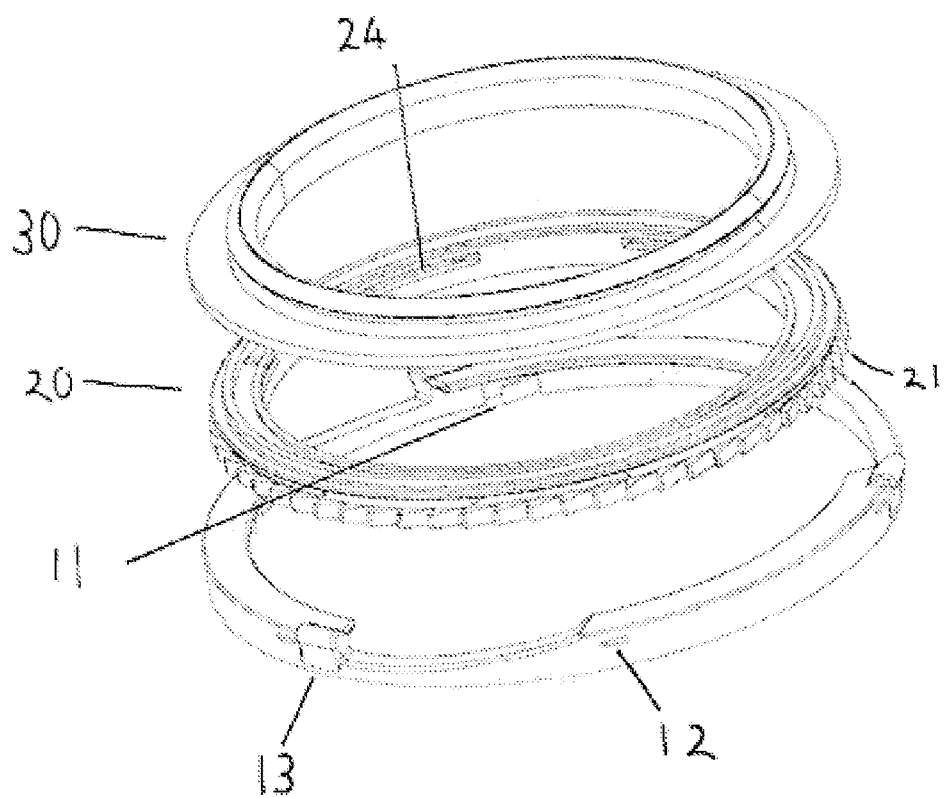
FIG. 3 shows an exploded view of the alignment member, the fixed base member and the coupling member of the sealing member according to the present invention.

FIG. 1 shows a sealing member of an ostomy body side member, where the sealing member has a round elastomeric collar 51 that is designed to seal around a stoma. The collar 51 is formed integrally with elastomeric sheets 52, 53. The collar has a set of coupling members 54 that are fixed to the inside of the elastomeric collar, onto which a set of strings 60 are attached, where the strings 60 along with the coupling member 54 form the adjustment member of the sealing member. The strings 60 are situated in between the elastomeric sheets 52, 53. The string may be made of a material such as nylon, polyester, PP, PE, polyamide or anything flexible but not extendible.

The elastomeric sheets 52, 53 are essentially circular in shape and have a fastening mechanism at the outer perimeter 55, 56 that attach onto the alignment member or the rotating ring 10 and fixed base member or ratchet ring 20, respectively.

The adjustment member is in the form of strings 60 which pass through a set of slots 24 on the fixed base member or ratchet ring 20. In these slots, there is a set of pins 70 for maintaining the position of the strings 60 in the slots, allowing the strings 60 to extend to the coupling members, and around which the strings 60 can run. The ratchet ring 20 has a set of positioning elements 23 into which these pins are arranged or fixed in. The ends of the strings are attached to a set of coupling members 12 on the alignment member or rotating ring 10, which couples the strings 60 to the alignment member 10.

In an alternative embodiment, the string 60 or the adjustment member may be a single string that is wound in such a way that the coupling members 12 on the alignment members and the coupling member 54 on the resilient sealing member are redirectional points for the string or U-shaped passageways and allow the string to be drawn there through, and each end of the string is fixed to the alignment member and the fixed base member, respectively. Thus, when the string is wound up by the alignment member, the length of the string inside the resilient sealing element is reduced and the diametrical dimensions of the stoma receiving orifice may be changed.

The fixed base member or ratchet ring 20 has a set of protrusions or teeth 21 that collectively make up the rack of the ratchet.

The fixed base member or ratchet ring 20 is fixed or joined to the user platform or the base plate (not shown) which may be attached to the ostomate.

The alignment member or rotating ring 10 has a set of coupling members 12 onto which the strings 60 attach. A set of interior depressions or indentations 11 makes up the pawls of the ratchet system. The alignment member or rotating ring 10 has a set of gripping means for the user to grip 13 and rotate the ring.

The elastomer sheet 50 is attached to the alignment member or the rotating ring 10 and/or the fixed base member or the ratchet ring 20 by a fastening mechanism 55, 56, which may be formed as protrusions or depressions in the resilient sealing member or the elastomer sheet 50 and a corresponding mating fastening mechanism on the alignment member 10 and the fixed base member 20. The elastomer sheet or the resilient sealing member 50 may be fastened to the alignment member and/or the fixed base member by means of gluing, welding, a clicking mechanism, a plug and socket arrangement or similar to ensure that the coupling of the resilient sealing member 50 is secure and does not constitute a weakness in the ostomy body side member.

A bag interface ring or coupling ring 30 may be joined to the fixed base member or the ratchet ring 20. This ring 30 is designed in such a way that the ostomy collection bag may be attached to it. The alignment member 10, the fixed base member 20 and the bag interface ring 30 may be made of a polymer, metal or similar materials that allow the members to be rigid and maintain their shape during application of tension, torque or other types of force during the use of the sealing member. Materials suitable for this are widely used in ostomy appliances and are well known by the skilled person in the art.

The alignment member 10, the fixed base member 20 and the bag interface ring 30 can be placed on top of each other or next to each other in such a way that the ratchet or the locking mechanism between the alignment member 10 and the fixed base member 20 ensures that the alignment member 10 and the fixed base member can selectively be locked in place and ensures that the members cannot be rotated relative to each other so that the resilient sealing member 50 or elastomer sheet is fixed at its diameter.

The invention claimed is:

1. An ostomy body side member having a sealing member where the sealing member comprises
    a fixed base member defining an opening having a first diameter,
    a resilient sealing element comprising a stoma receiving orifice defining an inner boundary where the inner boundary of the stoma receiving orifice has a second diameter that is smaller than the first diameter of the fixed base member,
    at least one adjustment member, comprising a string and coupling member, coupled between the fixed base member and the resilient sealing element, and
    an alignment member for adjusting the tension of the at least one adjustment member so that the diametrical dimensions of the stoma sealing orifice may be adjusted from a first diameter to a second diameter.

2. An ostomy body side member according to claim 1, wherein the first diameter of the stoma sealing orifice is larger than the second diameter of the stoma sealing orifice.

3. An ostomy body side member according to claim 1, wherein the first diameter of the stoma sealing orifice is smaller than the second diameter of the stoma sealing orifice.

4. An ostomy body side member according to claim 1, wherein the at least one adjustment member is adjustably coupled between the fixed base member and the resilient sealing element so that the tension of the adjustment member may be varied.

5. An ostomy body side member according to claim 1, wherein the fixed base member comprises locking means for fixing the position of the adjustment member relative to the base member.

6. An ostomy body side member according to claim 1, wherein there are two or more adjustment members coupled between the fixed base member and the resilient sealing element.

7. An ostomy body side member according to claim 6, wherein the two or more adjustment members are arranged substantially at equal radial distances from each other around the stoma sealing orifice of the resilient sealing element.

8. An ostomy body side member according to claim 1, wherein the fixed base member and the alignment member are in the form of a first ring and a second ring.

9. An ostomy body side member according to claim 1, wherein the fixed base member and the alignment member are arranged having a ratchet enabling click-wise rotation of the alignment member relative to the fixed base member.

10. An ostomy body side member according to claim 1, wherein the resilient sealing element is an elastomer membrane, sheet or tube.

11. An ostomy body side member according to claim 1, wherein the resilient sealing element is a silicone, rubber, thermoplastic elastomer, a Dow Corning 30 Shore A silicone type or any suitable elastomeric material.

* * * * *